US007205780B2

(12) United States Patent
Pasero et al.

(10) Patent No.: US 7,205,780 B2
(45) Date of Patent: Apr. 17, 2007

(54) MULTI-FREQUENCY CAPACITIVE MEASUREMENT DEVICE AND A METHOD OF OPERATING THE SAME

(75) Inventors: Eros Pasero, Turin (IT); Marco Riccardi, Occhieppo Inf. (IT); Tassilo B. Meindl, Turin (IT)

(73) Assignee: Fondazione Torino Wireless, Turin (IT)

( * ) Notice: Subject to any disclaimer, the term of this patent is extended or adjusted under 35 U.S.C. 154(b) by 0 days.

(21) Appl. No.: 11/228,065

(22) Filed: Sep. 16, 2005

(65) Prior Publication Data

US 2006/0192568 A1    Aug. 31, 2006

(30) Foreign Application Priority Data

Sep. 17, 2004   (EP)   .................... 04022196

(51) Int. Cl.
    *G01R 27/26*   (2006.01)
(52) U.S. Cl. .................. 324/667; 324/658; 324/663
(58) Field of Classification Search ............. 324/667, 324/658, 663, 664
    See application file for complete search history.

(56) References Cited

U.S. PATENT DOCUMENTS

| 3,046,537 | A |   | 7/1962 | Dow |
| 3,873,927 | A |   | 3/1975 | Overall .................... 328/4 |
| 4,058,766 | A | * | 11/1977 | Vogel et al. ............. 324/667 |
| 4,281,286 | A |   | 7/1981 | Briggs .................. 324/61 R |
| 4,654,598 | A | * | 3/1987 | Arulanandan et al. ...... 324/354 |
| 5,551,288 | A |   | 9/1996 | Geraldi et al. .......... 73/170.26 |
| 6,384,611 | B1 | * | 5/2002 | Wallace et al. ........... 324/671 |
| 6,695,469 | B2 | * | 2/2004 | Leonhardt ................ 374/25 |
| 6,963,205 | B2 | * | 11/2005 | Lundstrom et al. ........ 324/664 |

OTHER PUBLICATIONS

Ara N. Knaian, "A Wireless Sensor Network for Smart Roadbeds and Intelligent Transportation Systems," Jun. 2000 (200-06), Massachusetts Institute of Technology. (XP002313995).
European Search Report (EP 04 02 2196) dated Jan. 19, 2005.

* cited by examiner

*Primary Examiner*—Andrew H. Hirshfeld
*Assistant Examiner*—Marina Kramskaya
(74) *Attorney, Agent, or Firm*—McDonnell Boehnen Hulbert & Berghoff LLP

(57) ABSTRACT

A method and a system is provided that includes a multi-frequency generator supplying signals of at least three different frequencies to an electrode assembly, the capacitance of which is detected for a plurality of different frequency points. In this way, the capacitance of the electrode assembly, which is influenced by a substance present in the vicinity of the electrode assembly, may be reliably identified. Preferably, the conditions of a road surface may be reliably monitored.

39 Claims, 3 Drawing Sheets

MULTI-FREQUENCY CAPACITIVE MEASUREMENT DEVICE AND A METHOD OF OPERATING THE SAME

BACKGROUND

The present invention generally relates to a measurement system and a method for determining a change of capacitance of an electrode assembly that may be exposed to specified environmental conditions so that, for example, the presence of a specified substance results in a modified capacitance due to a change in relative permittivity.

In many fields, exact and fast information about the specific environmental conditions are required so as to initiate an appropriate response to the detected environmental conditions. For instance, an adequate assessment of the environmental conditions on road surfaces may significantly contribute to enhanced traffic safety, since corresponding decisions made by road administrators and surfaces may be based on this information. Moreover, information regarding the surface conditions may also be relayed to road users by means of broadcasting and electronic signs, thereby enabling the adaptation of speed limits driving style to currently prevailing road conditions. In particular, any information on road sections having ice or moisture formed thereon may help to significantly improve traffic safety. Thus, one of the key components of modern road information systems (RIS) is the monitoring of the current road surface conditions, wherein the detection of the presence of water, snow, ice and the beginning formation of ice, is one of the most important pieces of information for traffic safety. Based on the measurement data, critical information such as the possibility of aquaplaning or ice layers on the road surface can be determined in time and thus appropriate precautions may be taken.

The environmental conditions within a specified area may also be important in other fields such as ice formation on airplane wings, the gathering of reliable meteorology data, including the presence of ice, moisture, water, and the like on specific surfaces, as well as the detection of dangerous substances, such as fuels or ammoniac within specified areas. However, the efficiency of any system for detecting the presence or state of a specified substance strongly depends on the reliability of the measurement data, as, for instance, an erroneous indication of water instead of ice may even increase the probability of traffic accidents rather than provide for enhanced traffic safety. Moreover, a road information system may require the provision of a large number of individual surface detectors so that a high degree of reliability with respect to premature device failure, effort in view of maintenance as well as cost effectiveness of the individual sensor elements represent important criteria.

SUMMARY

Accordingly, it is an object of the present invention to provide enhanced sensor elements and methods for detecting a capacitive change of a sensor element, for instance in view of surface monitoring, with enhanced accuracy and reliability, especially with regard to water, snow, and ice detection on exposed surfaces and the detection of ice formation at an early stage.

According to one aspect of the present invention, the object is solved by a multi-frequency capacitive measurement device that comprises an electrode assembly configured to receive a sample substance for changing a capacitance of the electrode assembly. The device further comprises a multi-frequency generator coupled to the electrode assembly and configured to supply three or more signals, each having a different frequency, in a timely ordered manner. Additionally, the device comprises a sensing device connected to the electrode assembly and configured to determine a value indicative of the capacitance of the electrode assembly for each of the three or more different frequencies.

Generally, the capacitance of a capacitor, such as the capacitance of the electrode assembly, depends on the geometrical configuration such as distance, shape, and dimensions of corresponding surfaces of the electrode assembly and also depends on the relative permittivity of the material provided between the electrodes. The relative permittivity, in turn, depends on the temperature of the substance and a measurement frequency with which the capacitor is operated. Consequently, a reliable detection of a substance or a specified state thereof by means of a change in capacitance may not be reliably performed on the basis of one or two measurement points. Thus, the present invention provides a measurement device allowing the detection of a change in capacity of an electrode assembly at three or more different frequencies so as to provide a plurality of measurement points in the frequency domain in order to more precisely characterize the capacitance of the electrode assembly. Consequently, by means of the at least three measurement points in the frequency domain, the data may be more reliably compared with respective library data so as to identify the measured state of the electrode assembly in view of a specified reference state represented by the library data. For example, the relative permittivity of water at approximately −1° C. is substantially constant within a range from DC to about 1 kHz and decreases in the range of approximately 2 kHz-several hundred kHz. On the other hand, the relative permittivity of water of approximately 1° C. is substantially constant up to a frequency of approximately $10^9$ Hz and decreases within the range of $10^9$ to $10^{10}$ Hz. Thus, by means of the inventive multifrequency capacitive measurement device, a plurality of measurement points are taken in the frequency domain, which then enables a reliable identification of a specified substance, such as water with temperature +1° C. and water at temperature of −1° C. Hereby, a specified substance may be understood as a substance having a specified composition and specified state under specified environmental conditions. For instance, water at 1° C. at atmospheric pressure and ice at −1° C. at atmospheric pressure may be considered as two different specified substances. Hence, based on the plurality of measurement points in the frequency domain, the presence of, for example, water and ice may be detected at a high degree of reliability. Moreover, based on the plurality of measurement points, even the beginning formation of ice may be detected more reliably compared to conventional systems, which may be based on one or two measurement points.

In a further embodiment the sensing device comprises a charge detector configured to determine the charge accumulated on the electrode assembly for each of the at least three different frequencies. Hence, well-approved detector means, such as integrators, and the like may be used with the present invention, thereby enhancing cost effectiveness and reliability.

In a further embodiment, the sensing device comprises a sense capacitor and voltage measurement means, wherein the voltage measurement means is connected to the sense capacitor and is configured to determine a voltage across the sense capacitor.

Thus, the sensing device may have a configuration with a low number of inexpensive and readily-available approved components, thereby enhancing the reliability of the device.

Preferably, the voltage measurement means comprises an analog to digital (AD) converter so as to provide the measurement values indicative of the capacitance as digital values. Corresponding AD converters are well approved in the art and are available at a low price. For example, corresponding AD converters may be implemented in microcontrollers, which may also perform additional tasks within the measurement device, thereby rendering the device extremely reliable and space efficient.

In a further preferred embodiment, the frequency generator comprises a reference voltage source and a first controllable switch for periodically connecting the reference voltage source with the electrode assembly to provide the three or more signals of different frequencies. Consequently, the frequency generator may be provided as a simple and thus reliable electronic circuit, wherein the frequency generator may also advantageously be implemented within a microcontroller, which is typically configured to have a digital output that may be operated in a switched mode.

In a further embodiment, the voltage measurement means further comprises a second controllable switch for controllably connecting the sense capacitor with the electrode assembly. In this way, charge stored in the electrode assembly during the application of one of the three or more different signals may be transferred to the sense capacitor by using a circuit configuration of superior reliability and low component part count, thereby also contributing to device reliability and cost-effectiveness. Moreover, the sense capacitor may be selected so as to exhibit a well-known and large capacitance value compared to the capacitance of the electrode assembly, thereby facilitating the evaluation of the stored charge.

In a preferred embodiment, the three or more different frequencies range from approximately 50 Hz to at least several MHz. As previously explained, the change in capacitance of the electrode assembly caused by the presence of a specified substance of interest may be reliably detected and may be compared with corresponding library data so as to reliably identify the substance of interest. In particular, the frequencies selected so as to span the above-identified frequency range may enable the detection of the presence of water or ice on the electrode assembly in a highly reliable manner. It should be appreciated that according to the present invention any number of measurement points may be taken in the frequency domain within a range of several Hz to several MHz, depending on the substance to be identified by the progression of its relative dielectric constant with respect to the measuring frequency. For example, a plurality of respective reference data sets may be stored as a library referring to a plurality of substances of interest. For instance, if the measurement device of the present invention is to be used in a system for road surface monitoring, a plurality of substances of interest may represent a water, snow, ice or water containing a varying amount of de-icing substances, such as salt. Based on the precision of identifying a given substance as provided by the present invention due to the plurality of measurement points, there is even the possibility of indicating the presence or absence of a sufficient amount of de-icing substances when the measurement data indicate the beginning of the formation of ice. Similarly, the number of measurement points in the frequency domain and the measurement frequency range used may be adapted to any other substance of interest, such as the detection of fuel or other dangerous liquids within any region of interest.

In a preferred embodiment, the multifrequency capacitive measurement device further comprises comparator means configured to compare the value for each of the three or more different frequencies with a respective target value and to output an indication when each of the values matches its respective target value within a predefined tolerance range.

As previously explained, the values indicating the capacitance of the electrode assembly at a given frequency point may be compared with respective target values or library data so as to identify a substance of interest or a specified state thereof. Hereby, the measurement values may be manipulated in any required manner so as to provide them in a form that is suitable for comparison to the target values. For example, the measurement values may be transformed in corresponding values representing the relative permittivity of a material surrounding the electrode assembly when the target values are given as data representing the dielectric constants of the substance of interest with respect to frequency under specified environmental conditions. In other cases, the target values may be provided in any appropriate form so as to enable a direct comparison with the measurement values, thereby significantly facilitating the configuration of the comparator means. Preferably, the comparator means is implemented in a microcontroller, which may have stored therein the target values or which may have access to a separate unit providing the respective target values. For example, the target values may be supplied by an external source via a corresponding network so as to update or complete corresponding library data within the microcontroller or any other storage device in the multifrequency capacitive measurement device. Advantageously, the device may comprise a correspondingly equipped communication unit that allows receipt of corresponding target values over a wired network or a wireless network. In other embodiments, the communication unit may be configured to transmit data from the device to an external source via the network so that the measurement data may be evaluated at the external source, thereby providing the possibility of employing a large database containing a large number of different substances at different states. In particular, as previously explained, the target values may represent the relative permittivity of a material for at least two different temperatures at each of the three or more frequencies. In this way, the transition from water to ice and vice verse may be reliably detected and indicated.

In a further embodiment, the device further comprises a reference signal source configured to provide a reference signal to the sensing device, wherein the reference signal represents respective reference values for each of the three or more different frequencies. The reference signal indicative of a respective capacitance of the electrode assembly for each of the three or more different frequencies for a specified reference state.

By means of the reference signal source, a signal is available that indicates a specified reference state of the electrode assembly, which may then be used to enhance the accuracy of the measurement values obtained, since spurious signals and other effects affecting the electrode capacitance without being caused the sample substance may be reduced or eliminated. For example, the reference signal may be used to create a differential output signal of the sensing device, thereby enhancing the reliability of the measurement data.

In a further embodiment, the reference signal source is coupled to the sensing device and is configured to receive the measurement values indicative of the capacitance of the electrode assembly and to use the measurement values as the reference values when a state of the electrode assembly is designated as the reference state by a control signal.

In this way, the electrode assembly itself may be used as a source for creating a reference signal upon receipt of a control signal to thereby reduce or eliminate any deleterious effects. For example, when the environmental conditions for the electrode assembly are assessed to be appropriate for generating a reference signal, for instance, when it is assumed that the electrode assembly may not have formed thereon a specified substance, or a specified substance under well-known conditions is formed on the electrode assembly, an external source or an internal control unit may provide a corresponding control signal so as to activate a measurement cycle, the measurement data of which are then used as reference values for one or more future measurement cycles of the device. Since the condition of the electrode assembly is considered to be well known when being in the reference state, any other effects affecting the measurement process of the device may be reduced or eliminated, such as temperature drift, permanent contamination of the electrode assembly, and the like, since these effects are also, at least partially, represented by the reference values.

Advantageously, the reference signal source comprises a memory that is configured to store the reference values, which are preferably to be obtained as digital values. By storing the reference values, a desired number of actual measurement cycles may be performed on the basis of the established reference values. Moreover, the memory may be configured to store the reference values for a plurality of reference measurement cycles so as to establish a "history" of the reference states. In this way, the "evolution" of the measurement device may be estimated and may be used, for instance for evaluating the status of the device and the reliability of the device or specific components thereof. For example, an ongoing erosion of one or more of the electrodes of the assembly may result in a steady decrease or increase in the capacitance when being in the specified reference state, so that the maintenance or a replacement of a specific component may be initiated based on the assessment of the evolution of the reference signals. The evaluation of the status of the measurement device is particularly advantageous in a system requiring a high reliability, such as in a system for detecting ice formation on airplane wings, and is also particularly advantageous in systems comprising a large number of individual multifrequency capacitive measurement devices, which are equipped with respective communication units so as to transmit data to a central control station, since here the reliability of the entire system may strongly depend on the reliability of the individual devices. Thus, a prediction with respect to maintenance or expected remaining life time of the individual devices may significantly contribute to the overall reliability. Corresponding "status" data for assessing the status of the device may readily be established on the basis data gathered from a large number of devices and/or by corresponding test runs.

In a further embodiment, the sensing device further comprises an operational amplifier coupled to receive the reference signal and to output a differential signal to obtain the measurement value for each of the three or more different frequencies. In one preferred embodiment, the operational amplifier is connected so as to receive the voltage across the sense capacitor and the reference signal, and to output a difference thereof to the analog to digital converter.

By providing the operational amplifier in the above-specified manner, the signal path for conveying the signal from the electrode assembly to the AD converter is less prone to interferences and a signal level may be adjusted that is appropriate for the further signal processing by means of the AD converter.

In a further advantageous embodiment, the reference signal source further comprises a digital to analog converter that is connected so as to receive the stored digital reference values and to output to the operational amplifier an analog signal representing the stored digital values. Thus, the advantages obtained at the analog side of the circuit provided by the operational amplifier may be efficiently combined with digital signal processing, such as the storage of reference data for generating a reference signal, which may then be conveniently converted into an analog signal so as to establish the desired analog differential signal. Moreover, the DA converter may be advantageously implemented in a microcontroller, for instance in the form of an appropriately programmed digital output acting as a pulse width modulated output, or a plurality of suitably weighted digital outputs and the like.

In other preferred embodiments, at least one electrode of the electrode assembly is coated with an insulating material. Preferably, each of the electrodes in the assembly is coated with an insulating material layer. By providing an insulating material layer on at least one of the electrodes, the formation of a conductive path between the capacitively coupled electrodes via the substance of interest or any other materials is substantially prevented. Hence, the evaluation of the capacitance of the electrode assembly may be performed in a more reliable fashion.

In a further advantageous embodiment, the device further comprises a temperature sensor positioned so as to detect a temperature of the electrode assembly or of the vicinity of the electrode assembly. By providing the temperature sensor, additional environmental information may be gathered and used in characterizing and evaluating the measurement values indicating the capacitance of the electrode assembly. For instance, the knowledge of the temperature of a substance of interest may significantly enhance the process of identifying the substance on the basis of the frequency dependent capacitance values. Thus, substances or even the amount thereof may be identified in a more reliable fashion, thereby providing the potential for distinguishing between a greater number of different materials, such as water with different amounts of de-icing substances, and the like. Moreover, particularly in systems including a high number of individual devices, such as a road information system, the additional information regarding the temperature at or in the vicinity of electrode assembly, may be provided to a central station so as to complete additional meteorology data obtained by the weather forecast, thereby enabling to provide relevant traffic information with a higher "spatial resolution" compared to the meteorological data of the external source.

In a preferred embodiment, the device may comprise a control unit that is operatively connected to the frequency generator and the sensing device to control the operation thereof. Advantageously, the control unit, the frequency generator, and the sensing device are implemented in an appropriately programmed microcontroller, thereby significantly simplifying the construction of the device.

According to a further aspect of the present invention, a sensor system for determining environmental conditions comprises a plurality of multifrequency capacitive measurement devices according to any of the embodiments previously described and still to be described in the detailed description, wherein each measurement device comprises a communication unit configured to transmit data over a network. Moreover, the sensor system comprises a central station having a control unit and communication means configured to receive data over the network, wherein the control unit is configured to evaluate the state of the plurality of multifrequency capacitive measurement devices on the basis of the data received therefrom.

As previously explained, in many applications environmental conditions have to be detected across a distributed area, as is the case for road surface detecting systems, or in a system for detecting and monitoring the surface conditions of airplane wings at different locations, and the like. In these cases, the inventive system enables the monitoring of extended areas in a reliable manner, wherein the measurement data and/or the operational conditions of the individual measurement devices may be controlled and/or monitored by the central station. In some embodiments, the communication means of the central station and the communication units in the individual measurement devices are configured so as to enable the transmittance of measurement results to the central station. In this way, the plurality of measurement data may be evaluated more efficiently at the central station allowing the employment of the extended hardware and software resources thereof, since the measurement results of the individual devices may also be analysed with respect to the measurement results of other devices such as devices located in the vicinity of a specific device so that the consistency of the measurement results may be monitored. Moreover, the communication means and the communication units may be configured to allow transmission of data from the central station to one or more of the individual devices. For example, target values, e.g. library data in the individual devices may be updated on the basis of a decision made by the central station and appropriate target values may be transmitted to the individual devices. This may be advantageous when the storage capacity for target values within the devices is limited and global or local conditions may change and thus require a different set of target values. For example, during the summer period in a road information system the target values for water including a plurality of de-icing substances at temperatures below 0° C. may not be required and instead more accurate target values for water at higher temperatures and for varying amounts deposited on the electrode assembly may be transmitted to the individual measurement devices so as to more precisely detect the surface conditions during foggy or rainy weather.

According to a further aspect of the present invention, a meteorology measurement system comprises a multifrequency capacitive measurement device according to one of the previously-described embodiments. Moreover, the meteorology measurement system further comprises a control unit that is operatively connected to the multifrequency capacitive measurement device and is configured to evaluate data provided by the device. Moreover, display means are provided for displaying meteorology data.

According to the present invention, conventional meteorology measurement systems and stations may advantageously be equipped with the inventive measurement device so as to significantly extend the functionality of the meteorology measurement system. In particular, the measurement device, that is, at least the electrode assembly thereof, may be positioned so as to detect water, ice, snow, and possibly the various amounts thereof, on a specific measurement surface to obtain additional information. Thus, in combination with other sensor elements for indicating parameters such as temperature, humidity, wind, air pressure, duration of sunshine, and the like, a more accurate prediction and estimation of the weather condition may be achieved.

According to yet another aspect of the present invention, a method of determining the state of an electrode assembly is provided. The method comprises supplying at least three signals of different frequency to an electrode assembly that is in a state of interest. A measurement value is then determined that indicates a capacitance of the electrode assembly for each of the at least three different frequencies, and each measurement value is compared with a respective library value for each of the at least three different frequencies, wherein the library values represent a specified state of the electrode assembly for each of the at least three different frequencies. Finally, the state of interest is identified as the specified state when each measurement value matches the respective library value within a predefined tolerance range.

Hence, according to the present invention, a measurement value indicating the capacitance of the electrode assembly is obtained for three or more different frequencies, which are then compared with the library values so as to identify a specific state of the electrode assembly, such as the presence of a specified substance, as is also explained with reference to the inventive measurement device.

Moreover, as previously described, the library values may represent one or more specified substances under specified conditions, such as water for different temperatures under atmospheric conditions, wherein in some embodiments the library values may represent the relative permittivity of the substance of interest. The comparison of the measurement values with the library values may include any appropriate data manipulation, such as analog to digital conversion, digital to analog conversion, arithmetic calculations, intermediate data storage, and the like. In particular, the comparison of the measurement value with the library values and the identification of the state of interest may be performed on site, that is, by a measurement device comprising the required components in a stand alone configuration, or may be performed remotely, for instance, by transmitting the measurement values by a corresponding network, by wire or wireless, to an appropriately equipped analyzing station. For example, the components on the measurement site may include the electrode assembly in combination with a frequency generator, a sensing device, and communication means, so as to communicate the measurement results to the remote station, which may employ powerful hardware and software resources so as to perform the comparison with library values and estimate the measurement values.

In another embodiment, the method comprises exposing the electrode assembly to an environmental condition to receive at least one substance of interest, wherein the library values represent the state of the electrode assembly having applied thereon the at least one substance in a predefined state.

Thus, the inventive method is most advantageous in determining the presence and/or the state of a substance of interest that may be deposited on the electrode assembly during specified environmental conditions. Hereby, the library values represent the substance of interest in a well-known predefined state so that this state may be readily identified upon comparing the measurement values with the library values. As previously explained, according to the present invention the comparison takes place on the basis of at least three different frequencies so as to allow a reliable identification of a specified substance. Advantageously, the library values represent a relative permittivity of the substance of interest under specified conditions for each of the at least three different frequencies.

In one preferred embodiment, the method further comprises establishing a library of data representing a relative permittivity at each of the at least three different frequencies for at least the substance of interest for a plurality of different states of the substance. For example, data representing the relative permittivity of water at different temperatures under atmospheric pressure may be gathered and may be prepared as a library of data that may then be used so as to compare measurement data and identify a corresponding state of the electrode assembly when exposed to water. Similarly, library data may be established for a plurality of different substances, such as water with different amounts of specific ingredients like salt and the like, or library values may be obtained for fuels, ammoniac, and the like so as to identify these substances upon deposition on the electrode assembly.

In a preferred embodiment, the method further comprises applying the substance having a specified state on the electrode assembly, determining a reference measurement value indicating a capacitance of the electrode assembly for each of the at least three frequencies, and storing the reference measurement value or a value representing the same as library data for the specified state.

In this way, the library data may be created by the measurement device itself using the same hardware components as are also used during actual measurements, thereby providing the potential for reducing the effort required for signal processing during the data acquisition and assessment, since the library data may be stored in any appropriate form and state during the signal processing and thus in the same form and state as the actual measurement data. For instance, the measurement readings indicating the capacitance of the electrode assembly may be directly used as library data and may be stored so that in further actual measurement cycles these library values may directly be compared with the measurement values. Consequently, neither the measurement values nor the library values have to be transformed into a specific data format, such as numbers directly representing the relative permittivity, so that the signal processing and the comparison may be performed based on a signal format that is convenient for the signal processing. Moreover, any inherent effects of the measurement apparatus on the measurement data may not need to be taken into account as the library values are also affected by the same effects.

In a preferred embodiment, determining the measurement value indicating a capacitance of the electrode assembly for each of the at least three different frequencies comprises a) charging the electrode assembly with a signal having one of the at least three different frequencies for a predefined time period, b) determining the charge stored on the electrode assembly, and c) repeating the steps a) and b) for each of the at least three different frequencies.

Consequently, an accurate indication of the capacitance of the electrode assembly may be obtained by determining the total charge stored thereon during the application of a predefined pulse train. Preferably, the predefined time period for each of the at least three different frequencies is adjusted by supplying a signal including a predefined number of pulses. By providing the signals with a specified number of pulses, both the frequency of the signal as well as the predefined time period for charging the electrode assembly may be readily controlled by means of a square wave generator or by an appropriately programmed digital output of a microcontroller.

In a preferred embodiment, the charge stored on the electrode assembly is determined by connecting the electrode assembly with a sense capacitor after the predefined time period has elapsed and by determining a voltage across the sense capacitor. In this way, the charge stored on the electrode assembly may be determined with a reduced number of electronic components, wherein advantageously the capacitance of the sense capacitor is selected significantly higher than any expected value for the capacitance of the electrode assembly, thereby minimizing the influence of the sense capacitor on the measurement readings. The connection of the sense capacitor to the electrode assembly may be accomplished by a fast semiconductor switch, such as a field effect transistor or the like, which may be controlled by the digital output of a microcontroller without requiring further components, thereby rendering the control of the voltage measurement highly efficient.

In a further embodiment, determining the measurement value indicating the capacitance of the electrode assembly for each of the at least three different frequencies comprises a) supplying a signal having one of the at least three different frequencies and a specified amplitude to the electrode assembly via a specified resistor, b) determining a voltage across the electrode assembly, and c) repeating steps a) and b) for each of the at least three different frequencies. Hence, the capacitance of the electrode assembly may form a frequency dependent voltage divider with the specified resistor so that the capacitance of the assembly may be determined on the basis of the voltage drop and the specified amplitude for each of the at least three different frequencies. For example, a microcontroller operated at a stable supply voltage may supply via an appropriately programmed digital output a signal of specified frequency and duty cycle so that based on these parameters and the actually determined voltage drop at the electrode assembly the capacitance may be determined. Preferably, the voltage drop is determined by means of an integrating filter that may comprise a resistor and a capacitor coupled in the form of a low pass filter, wherein the voltage across the filter capacitor is measured as the desired voltage drop.

According to still a further aspect of the present invention, a method comprises providing a plurality of electrode assemblies and determining a state of each of the electrode assemblies according to any of the methods described above or defined in the appended claims and the following detailed description. Thus, based on this method a plurality of measurement data may be collected so as to "cover" a specified area with a desired spatial resolution. For example, this method may be advantageously employed in combination with a road information system, monitoring systems for environmental conditions, surface monitoring of airplane wings, ship hulls, rocket hulls, and the like. In a preferred embodiment, the method further comprises communicating the measurement values to a central station, wherein the steps of comparing and identifying are performed in the central station. Hence, the measurement data may be processed and evaluated in a highly efficient manner due to the superior hardware and software resources that are typically available in the central station. For example, a voluminous library of library data may be available in the central station, wherein a high processor power may enable the comparison of the measurement results, even for a large number of individual electrode assemblies, to be compared with the library data so as to precisely determine the substance and state thereof provided on one or more of the plurality of electrode assemblies. Moreover, in some embodiments, a bi-directional data transfer between the electrode assemblies and the central station may be established so that the operation and/or the status of any hardware components required for sensing the state of the electrode assemblies may be monitored and/or controlled by the central station. In other embodiments, the electrode assemblies and the associated hardware components may be equipped to temporarily store measurement results, which may then be retrieved by the central station as required. In particular, a reference measurement may be initiated by the central station so as to assess the current status of the electrode assembly, wherein the initiation of the reference measurement may be based on additional information, such as meteorology information, a temperature signal, and the like. In this way, relatively reliable reference data may be gathered, for instance for a road information system, which may be stored in order to obtain an indication of the performance of the electrode assembly over time.

Further preferred embodiments of the present invention are described in the appended claims and will also be described with reference to the accompanying drawings.

DETAILED DESCRIPTION OF A PREFERRED EMBODIMENT

Figure 1A:
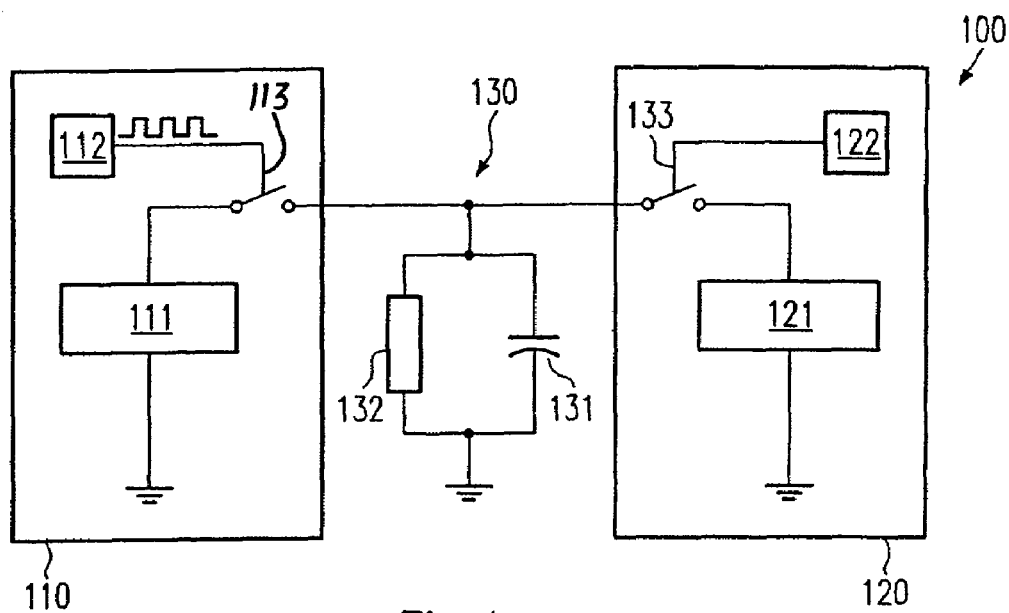
FIG. 1a schematically shows a circuit diagram of a basic embodiment of a capacitive measurement device in accordance with one illustrative embodiment of the present invention.

FIG. 1a schematically shows a capacitive measurement device 100 comprising a frequency generator 110, a sensing device 120, and an electrode assembly 130. The electrode assembly 130 may comprise two or more individual electrodes that are configured and positioned so as to define a specified capacitance between at least two individual electrodes for a predefined condition of the electrode assembly 130. That is, the individual electrodes of the assembly 130 include conductive portions defining a specified capacitor surface positioned such that a predefined distance is defined therebetween. As is well known, the effective capacitance of two conductive surfaces positioned close to each other is defined by the geometrical configuration, the size of the effective surface area, the distance between the surface areas, and the permittivity of the space enclosing the surface areas. For instance, the electrode assembly 130 may comprise at least one pair of plate like electrodes having a well-defined geometric configuration and being supported by a corresponding housing or support such that the electrode assembly 130 is positionable to receive a substance of interest on at least one exposed surface portion. Advantageously, at least one of the exposed surface portions of the individual electrodes of the assembly 130 is coated by an insulating material layer so as to eliminate or at least reduce the probability for establishing a conductive path between individual electrodes. For instance, if the electrode assembly 130 is provided in the form of a plate-like electrode pair with respective lead wires, one or both electrodes may be completely insulated so that even if the total space between the electrode plates is filled with a conductive medium, such as water, ice, snow and the like, a short circuit between the electrodes is avoided. In the circuit diagram, the electrode assembly 130 is represented by a capacitor 131 and a high ohmic resistor 132 connected in parallel to the capacitor 131. In particular, when the electrode assembly 130 has formed a corresponding insulating layer on respective electrodes, the resistor 132 may be considered as substantially constant, even if various substances are deposited on the electrode assembly 130. It should be appreciated, however, that any other influences such as temperature, material wear, and the like may affect the value of the resistor 132 as well as the capacitance of the capacitor 131 in a specified state of the electrode assembly 130. Corresponding minor fluctuations of the resistor 132 and the capacitor 131 may, however, be readily compensated for, as will be described later on. The frequency generator 110 is configured to provide signals with at least three different frequencies, wherein in preferred embodiments the frequency generator 110 is configured to provide signals with frequencies in the range of approximately 50 Hz to several hundred kHz or even up to several MHz. For example, the frequency generator 110 may be configured to produce signals with a frequency of 50 Hz, 100 Hz, 1 kHz, 20 kHz, 100 kHz and 500 kHz and more. In the embodiment shown in FIG. 1a, the frequency generator 110 comprises a reference voltage source 111 connected to a controllable switch 113 that is connected to a control unit 112. The controllable switch 113 may comprise a field effect transistor whose gate is connected to the control unit 112, which, in turn, may be adapted to deliver a gate signal of a specified frequency and duty cycle so as to correspondingly connect the reference voltage source 111 to the electrode assembly 130 according to one of the plurality of frequencies that may be produced by the frequency generator 110. It should be appreciated that the frequency generator 110 as shown in FIG. 1a may produce signals of different frequencies of the square wave type, since the required hardware configuration may then be obtained by a low number of components. It should be appreciated, however, that any other circuit producing other types of signals may be appropriate as long as three or more frequencies may be supplied to the electrode assembly 130. In particular embodiments, as will also be described with reference to FIGS. 1d–1f, the frequency generator 110 may be implemented in a microcontroller and the controllable switch 113 may be provided in the form of a digital output of the microcontroller.

The sensing device 120 may be configured in the embodiment shown in FIG. 1a so as to determine the charge stored on the capacitor 131 after a signal of predefined frequency has been applied for a predefined time period. Consequently, the sensing device 120 may comprise any charge sensitive measurement device 121, such as an integrator and the like, as is well known in the art. In one particular embodiment, the sensing device 120 may comprise a controllable switch 133 connected to a control unit 122 that is configured to activate the switch 133 so as to connect the charge detector 121 with the electrode assembly 130. For example, the switch 133 may be provided in the form of a field effect transistor controlled by the unit 122, wherein the unit 122 may represent a portion of a microcontroller, such as a digital output driven by a corresponding software program running in the microcontroller.

During operation of the device 100, a specified substance may have been deposited on the electrode assembly 130 or at least a portion thereof, thereby influencing the capacitance of the capacitor 131. In the following, it is referred to water as a substance of interest, wherein it should be appreciated that the present invention may be readily applied to any substance that leads, after deposition on the electrode assembly 130, to a measurable change of capacitance.

Figure 1B:
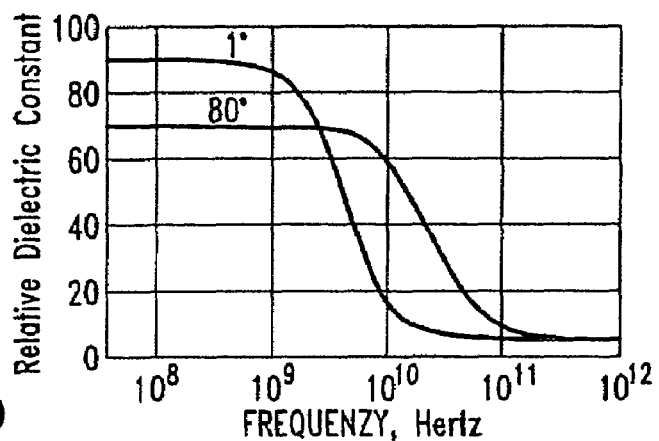
FIGS. 1b and 1c depict plots of the characteristic of a relative dielectric constant of water when acting as a dielectric of a capacitor operating at various frequencies for temperatures above the freezing point (FIG. 1b) and below the freezing point (FIG. 1c).
Figure 1C:
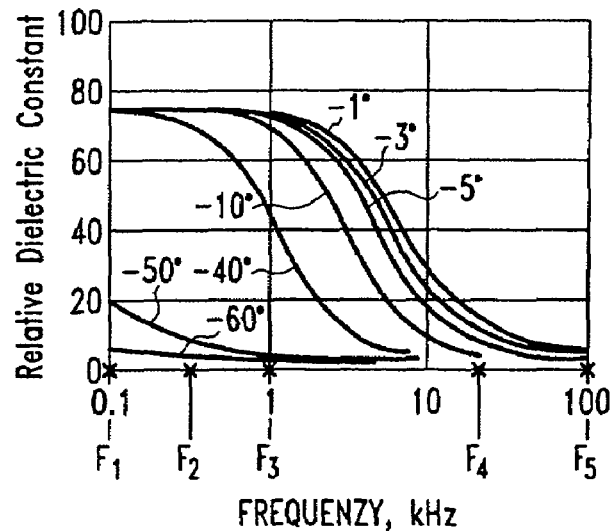

FIGS. 1b and 1c schematically show the progression of the relative dielectric constants of water versus the measurement frequency for a plurality of different temperatures. FIG. 1b schematically shows the behaviour for the liquid phase of water, while FIG. 1c illustrates the formation of ice and snow and represents the solid state of water. As can be seen from FIG. 1b, liquid water has a moderately high dielectric constant of approximately 90 for a temperature of 1° C. and of approximately 70 at a temperature of 80° C. Consequently, introducing water in close proximity to the electrode assembly 130 may significantly influence the capacitance of the capacitor 131, since the capacitance is directly proportional to the relative dielectric constant.

FIG. 1c schematically shows similar curves for water below the freezing point, wherein it is evident that ice or snow with temperatures of −1° C. to −40° C. have approximately the same dielectric constant compared to water of 80° C. and below, so that a corresponding measurement of the capacitance of the capacitor 131 at constant current or low frequencies may not allow to distinguish between hot water and ice and snow. Consequently, according to the present invention a plurality of measurement signals are applied to the capacitor 131 with a plurality of different frequencies so that a plurality of measurement data is obtained for at least three different frequencies and preferably more, which may allow the distinction between different substances or different conditions of the same substance. FIG. 1c shows a plurality of measurement points F1 . . . F5 in the frequency domain that may be selected so as to obtain a plurality of measurement data representing the capacitance and thus the dielectric constant of a substance disposed on the electrode assembly 130. It should be appreciated that the frequency values F1 . . . F5 are of illustrative nature only and other values, especially more than the values shown, may be selected in conformity with the present invention.

The frequency generator 110 is then operated to provide a plurality of different signals corresponding to a plurality of different frequencies, such as the frequencies F1 . . . F5, wherein each of the different signals is applied to the electrode assembly 130 for a predefined time period. For example, in the embodiment shown the control unit 112 may activate the switch 113 periodically to produce a predefined number of output pulses having a specified duty cycle, for instance a duty cycle of 50 percent. This square wave signal is then applied to the electrode assembly 130 and leads to the storage of a specified amount of charge on the capacitor 131 after the electrode assembly 130 is disconnected by the switch 113. At this time, the control unit 122 may activate the switch 123 so as to sense the charge stored on the capacitor 131, which is indicative of the capacitance of the capacitor 131. Typically, the charge detector 121 comprises a sense capacitor, wherein in a preferred embodiment the charge detector 121 may comprise a capacitor of well defined capacitance that is essentially larger than the capacitance of the capacitor 131 for any expected substance deposited thereon. Hence, in this situation the capacitance of the capacitor 131 may be evaluated by determining a voltage across the sense detector 121 and the voltage provided by the reference voltage source 111. The above procedure may be repeated for any of the desired frequencies, such as the frequencies F1 . . . F5 and the correspondingly obtained measurement values indicating that the capacitance of the capacitor 131 may then be used to compare these values with corresponding library data that may be obtained from information, such as the diagrams of FIG. 1b and 1c. It should be appreciated that corresponding library data may be easily obtained from publicly accessible sources such as databases and the like.

In other embodiments, corresponding library data may be established on the basis of measurement results obtained by the device 100 itself or a corresponding device in that a well known substance under well defined conditions is applied to the electrode assembly 130 and a measurement sequence is carried out, as is described above. The corresponding measurement values may then be used as library data for the specified substance under the specified conditions. Thereafter, a plurality of different conditions and/or different substances may be measured so as to establish a plurality of library data, which may then be used for a comparison with actual measurement data so as to identify a specific substance and/or the status thereof. In this way, a further signal processing of measurement values is not required, since the measurement values may directly be compared with other measurement values, acting as library data, so that signal processing and data manipulation are significantly simplified. It should be appreciated, however, that a further data processing for relating the measurement results to calibrated library data may be performed, even if the library data actually used during the measurement runs are obtained by the apparatus 100 as measurement results, since then the performance of the device 100 may be monitored when a corresponding recalibration of the library data is performed on a regular basis by means of "calibrated" data, such as the data of the curves if FIGS. 1b and 1c.

Figure 1D:
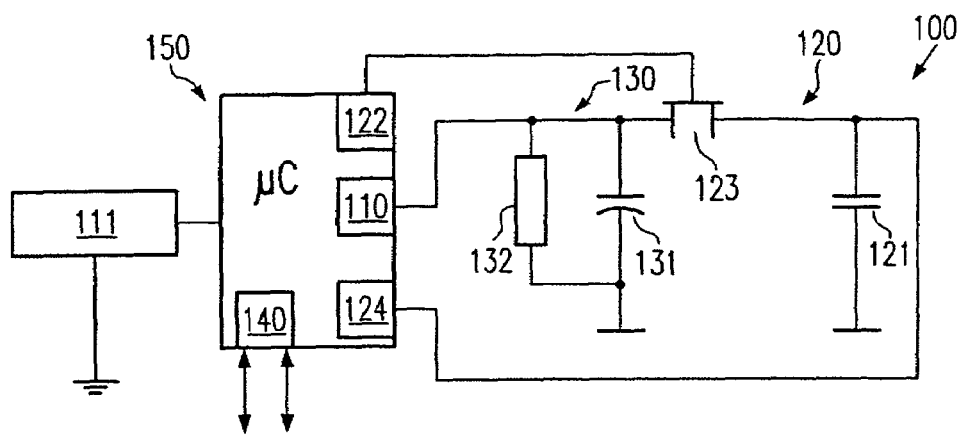
FIGS. 1d–1f schematically show circuit diagrams of various embodiments of the measurement device comprising a microcontroller.

FIG. 1d schematically shows the multifrequency capacitive measurement device 100 according to further illustrative embodiments. The device 100 further comprises a microcontroller 150 having implemented therein various functions in the form of hardware and/or software components so as to provide for the functionality, at least partially, of the frequency generator 110 and the sensing device 120. In the embodiment shown, the sensing device 120 comprises a sense capacitor 121 as the charge detector, which is coupled to a voltage measuring means 124, which may be provided in the form of an AD converter of appropriate resolution. For instance, the voltage measuring means 124 may be implemented in the microcontroller 150, as presently many microcontrollers are available having AD converter circuitry with resolution from 8 bits to 16 bits incorporated therein. Moreover, the controllable switch 123 of the sensing device 120 is provided in the form of a field effect transistor whose gate is connected to the control unit 122 provided in the form of a software program in combination with a specified digital output of the microcontroller 150. Moreover, the reference voltage source 111 may be provided in the form of a stabilized power supply for the microprocessor 150.

The operation of the device 100 as shown in FIG. 1d may be performed in a similar fashion as described with reference to FIGS. 1a–1c, wherein particularly the processing of measurement data and/or library data is simplified due to the AD conversion of the voltage measured across the sense capacitor 121. Based on the voltage measurement readings, the microprocessor 150 may perform a comparison with corresponding library data, which may be stored within the microprocessor 150 or which may be supplied to the microcontroller 150 via a corresponding interface 140. The interface 140 is to represent any communication means that is appropriate to communicate with an external source so as to provide measurement results to the external source or receive library data and/or control signals for controlling the measurement operation of the device 100. For example, the external source may represent a memory device containing the library data.

In some embodiments, it may be advantageous to provide a reference signal along with the measurement values obtained from the sensing device 120 so as to compensate for or reduce any internal or external effects that are not created by the substance of interest on the electrode assembly 130. Thus, a second electrode assembly (not shown) may be provided with corresponding hardware components so as to provide corresponding measurement values indicating the capacitance of the second electrode assembly, wherein the second electrode assembly is positioned so as to remain in a well-defined state, substantially without being exposed to the substance of interest. In this way, any influences that are not caused by the substance of interest may affect the electrode assembly 130 and the second electrode assembly in a similar fashion so that corresponding effects on the measurement results may be cancelled or at least significantly reduced.

Figure 1E:
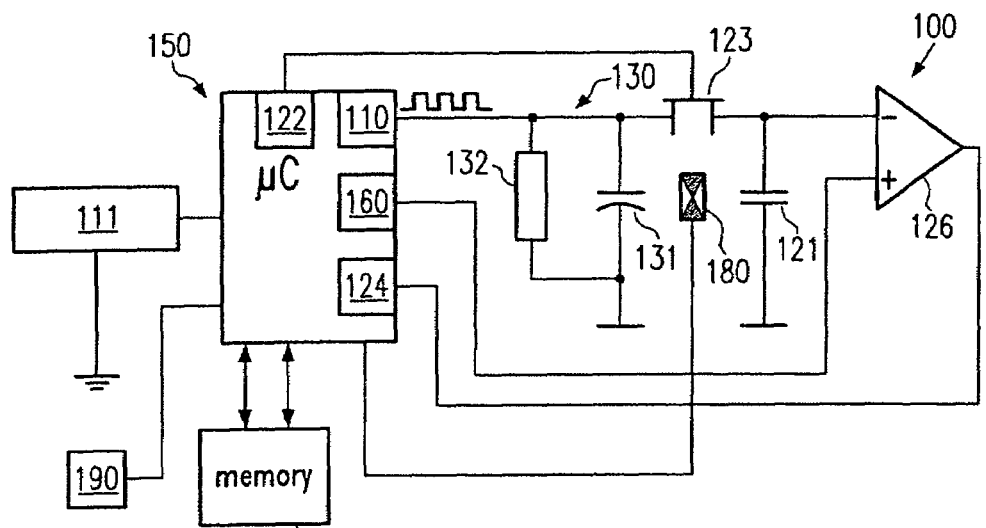

FIG. 1e schematically shows a further embodiment of the device 100 including a reference signal source without requiring a second electrode assembly. The device 100 comprises an operational amplifier 126 that is connected with its input to the sense capacitor 121 and to a reference signal source 160, which in the embodiment shown is represented by a portion of the microcontroller 150. For example, the reference signal source 160 may comprise a DA converter so as to provide an analog signal on the basis of digital values supplied thereto. The device 100 may further comprise a memory device 170 connected to the reference signal source 160.

During operation, the electrode assembly 130 may be in a well-specified state, for example, a well-specified substance may be provided thereon or the electrode assembly may substantially be completely devoid of any substance so that the electrode assembly 130 may be expected to have a well-defined capacitance, and a measurement sequence may be started wherein the reference signal source 160 may provide a neutral or constant signal so as to not affect the measurement results obtained. The corresponding measurement results may then be stored in the memory device 170 as reference values that may then be used in subsequent actual measurement cycles to compensate for device fluctuations and systematic drifts. The reference values may be established on a regular basis when it may be expected that the electrode assembly 130 is in a predefined state, or may be established on demand, for instance upon application of a control signal provided by an external source or by the microcontroller 150 when detecting a certain condition. The reference values may be stored so as to monitor the progression of the reference values over time, wherein in some embodiments certain criteria may have been established so as to assess the status of the device 100 in correlation to the progression of the reference values. In particular, the microcontroller 150 may indicate an invalid status when one or more reference measurements do not match one or more of "validity" criteria that may be defined as specified threshold ranges. For example, a degradation of the insulating material coating the electrode assembly 130 may lead to a significant change of the reference values over time, thereby also rendering the actual measurement results less reliable and hence the device 100 may indicate an invalid status or at least may give a notification that the measurement results may be considered with caution. A corresponding monitoring of the device status is advantageous in highly sensitive applications and/or in applications requiring a large number of devices 100 so that the device status of the individual devices may effectively be estimated.

Moreover, the device 100 may comprise one or more additional sensor elements, such as a temperature element 180 that is connected to a corresponding control unit, which in the present example is represented by the microcontroller 150. The additional information gathered by the sensor 180 may enhance the accuracy in detecting specific substances so as to obtain a finer "resolution" in comparing the measurement results with corresponding library data.

In other embodiments, the device 100 including one or more additional sensor elements 180 may represent a meteorology system, the functionality of which is significantly extended by the electrode assembly 130 in combination with the sensing device 120 and the multifrequency generator 110. In this case, the device 100, acting as a meteorology system, may also comprise display means 190 connected to the microcontroller 150 so as to display any information on the basis of measurement results obtained from the electrode assembly 130 and/or the sensor elements 180.

Figure 1F:
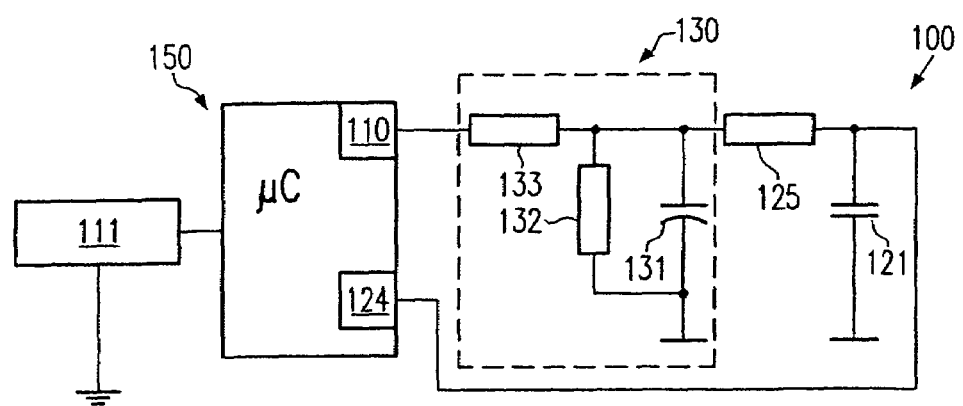

FIG. 1f schematically shows the device 100 in which the sensing device 120 is simplified in that the switch 123 may be omitted and may be replaced by a high ohmic resistor 125 that forms, in combination with the sense capacitor 121, a low pass filter. Moreover, the electrode assembly 130 may comprise a resistor 133 that forms, in combination with the capacitor 131, a frequency dependent voltage divider. During operation of the device 100, signals of specified frequency and amplitude, such as a square wave signal of well-known amplitude and duty cycle, are supplied to the electrode assembly 130, wherein a corresponding voltage is established across the capacitor 131, which depends on the predefined frequency, amplitude and duty cycle, and the value of the resistor 133. Since the resistor 133 having a well-defined resistance may easily be incorporated into the electrode assembly 130 or at any appropriate location within the signal path, the capacitance of the capacitor 131 may be determined by sensing the voltage drop at the capacitor 131. To this end, the voltage may be measured at the sense capacitor 121, wherein the specific value is not critical as long as the resistor has a sufficiently high value and the capacitor appropriately smoothes the signal supplied to the capacitor 131. Hence, the capacitance of the capacitor 131 may be determined while a signal of defined frequency is applied without requiring specified control over the number of pulses and of any switches controlling the operation of the voltage measurement. For measurements with signals of very low frequency, the operation of the AD converter 124 may be timely related to the low frequency pulses supplied by the frequency generator 110 and a plurality of measurements may be performed within each cycle, thereby obtaining a moderately precise average value. It should be appreciated that the embodiment shown in FIG. 1a may be readily combined with the components shown in FIG. 1e, such as the operational amplifier 126, the reference signal source 160 and/or the additional sensor element 180.

Figure 2:
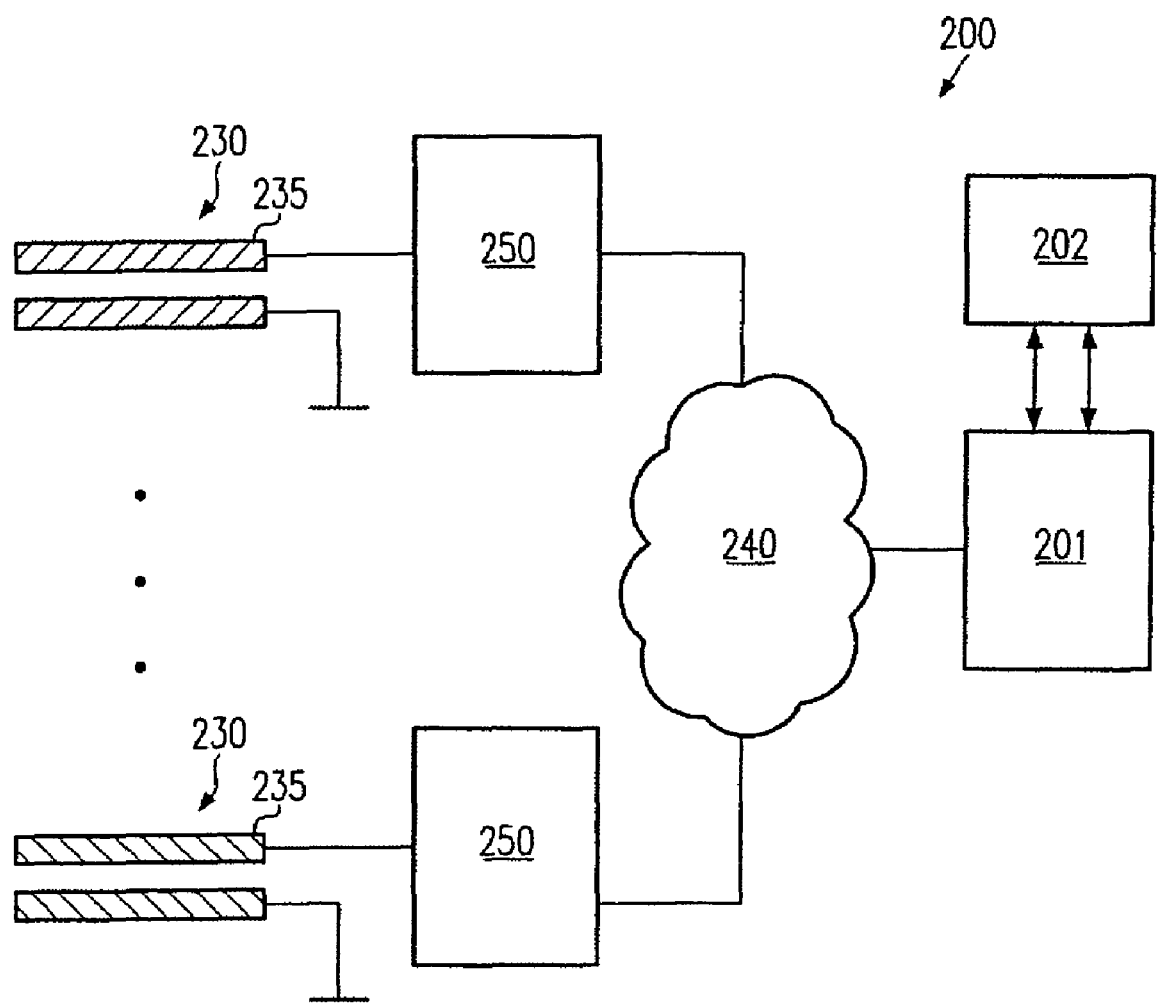
FIG. 2 schematically shows a system including a plurality of capacitive measurement devices connected to a central station.

FIG. 2 schematically shows a system 200 comprising a plurality of electrode assemblies 230 positioned and formed to receive a substance of interest. In particular, the electrode assemblies 230 may comprise at least one pair of electrodes having insulated surface portions 235 that define a specific capacitance of the electrode assemblies 230. The electrode assemblies 230 are each connected to respective hardware and software resources 250, which enable to perform a multifrequency capacitance measurement, as is described with reference to FIGS. 1a–1f. Moreover, the hardware and software resources 250 also include communication units that are configured to communicate with a central station 201 via a network 240. The network 240 may represent any appropriate network for wired or wireless communication. The central station 201 may be configured to monitor and/or control the operation of the individual hardware and software resources 250 and may also be configured to receive measurement results from the individual resources 250 so as to determine the presence and/or the status of a substrate of interest deposited on the individual electrode assemblies 230. In one particular embodiment, the system 200 may represent a system for gathering information on road surface conditions in which the individual electrode assemblies 230 are positioned at respective sites of a road of interest so as to determine the presence of water, ice, snow, and the corresponding status of these substances, such as the start of ice formation and the like. In other embodiments, the system 200 may represent a multisensor system for detecting specific substances on critical areas such as airplane wings and the like. In one particular embodiment, the hardware and software resources 250 and/or the central station 201 are configured to estimate the device status of the individual electrode assemblies 230 and/or the status of their hardware and software resources 250, for instance on the basis of reference measurement data, as is previously explained.

In other embodiments, the central station 201 may be connected to external sources so as to receive or provide information therefrom or thereto, such as meteorology information, technical information and the like.

As a result, the present invention provides for a novel multifrequency capacitance measurement system that allows determination of the capacitance of an electrode assembly on the basis of three or more frequencies, thereby providing the potential for determining the presence and the characteristics of a substance of interest in a reliable manner. Advantageously, the system and the method may be employed by companies controlling and managing roads and highways, thereby providing the ability to monitor the road surface conditions to improve safety and reduce costs by avoiding unnecessary deployment of de-icing substances on the road surface. Moreover, the capabilities of meteorological stations may be extended by the functionality provided by the present invention so as to allow the reliable detection of the surface conditions of an exposed surface. Moreover, in many industrial fields the detection of polar liquids such as water, fuels, or ammoniac is required, wherein the high degree of hardware reliability and low cost render the present invention a very attractive approach. Moreover, the apparatus of the present invention may be provided in the form of a low volume device so as to facilitate installation on corresponding measurement sites, such as road surfaces. The complexity of the total configuration is low, thereby ensuring a reliable system over a long operating time, wherein power consumption may be kept at a low level so that a continuous monitoring of specific conditions without an external power supply is feasible. Moreover, due to the multifrequency measuring concept, an extended sensitivity is achieved that not only allows detection of the presence of water or ice, but also enables the detection of the thickness of an ice layer or water layer and a precise monitoring of ice formation.

The invention claimed is:

1. A multi-frequency capacitive measurement device comprising:

an electrode assembly configured to receive a measurement substance for changing a capacitance of said electrode assembly, a multi-frequency generator coupled to said electrode assembly and configured to supply in a timely ordered manner three or more signals each having a different frequency, and a sensing device connected to said electrode assembly and configured to determine a value indicative of the capacitance of said electrode assembly for each of said three or more different frequencies, further comprising a reference signal source configured to provide a reference signal to said sensing device, said reference signal representing respective reference values for each of said three or more different frequencies and being indicative of a respective capacitance of said electrode assembly for each of the three or more different frequencies for a reference state.

2. The multi-frequency capacitive measurement device of claim 1, wherein said sensing device comprises a sense capacitor and voltage measurement means connected to said sense capacitor and configured to determine a voltage across the sense capacitor.

3. The multi-frequency capacitive measurement device of claim 2, wherein said voltage measurement means comprises an analog to digital converter to provide said values as digital values.

4. The multi-frequency capacitive measurement device of claim 1, wherein said frequency generator comprises a reference voltage source and a first controllable switch for periodically connecting said reference voltage source with said electrode assembly to provide said signals having said three or more different frequencies.

5. The multi-frequency capacitive measurement device of claim 2, wherein said voltage measurement means further comprises a second controllable switch for controllably connecting said sense capacitor with said electrode assembly.

6. The multi-frequency capacitive measurement device of claim 1, wherein said three or more frequencies are selected from approximately 50 Hz to at least several MHz.

7. The multi-frequency capacitive measurement device of claim 1, further comprising comparator means configured to compare the value for each of the three or more different frequencies with a respective target value and output an indication when each of said values matches its respective target value within a predefined tolerance range.

8. The multi-frequency capacitive measurement device of claim 7, wherein said respective target values represent a relative permittivity of a substance of interest at each of said three or more frequencies.

9. The multi-frequency capacitive measurement device of claim 8, wherein said respective target values represent the relative permittivity of said substance of interest at said three or more frequencies for two or more different temperatures of said substance of interest.

10. The multi-frequency capacitive measurement device of claim 9, wherein said respective target values represent relative permittivities of at least two substances of interest at said three or more frequencies.

11. The multi-frequency capacitive measurement device of claim 9, further comprising a temperature sensor.

12. The multi-frequency capacitive measurement device of claim 1, wherein said reference signal source is coupled to said sensing device and configured to receive said values indicative of the capacitance of the electrode assembly and use said values as the reference values when a state of said electrode assembly is designated as the reference state by a control signal.

13. The multi-frequency capacitive measurement device of claim 12, wherein said reference signal source comprises a memory configured to store said reference values obtained as digital values.

14. The multi-frequency capacitive measurement device of claim 1, wherein said sensing device further comprises art operational amplifier coupled to receive said reference signal and to output a differential signal to obtain said value for each of the three or more different frequencies.

15. The multi-frequency capacitive measurement device of claim 14, wherein said operational amplifier is connected to receive the voltage across said sense capacitor and said reference signal and to output said differential signal to said analogous to digital converter.

16. The multi-frequency capacitive measurement device of claim 15, wherein said reference signal source further comprises a digital to analog converter connected to receive said stored digital values and output to said operational amplifier an analogous signal representing said stored digital values.

17. The multi-frequency capacitive measurement device of claim 1, wherein said frequency generator and said sensing device are implemented in a micro-controller.

18. The multi-frequency capacitive measurement device of claim 1, wherein each electrode in said electrode assembly is coated with an insulating material layer.

19. The multi-frequency capacitive measurement device of claim 1, further comprising communication means configured to transfer data to an external source.

20. A sensor system for determining environmental conditions, comprising:
- a plurality of multi-frequency capacitive measurement devices, wherein each measurement device includes:
  - an electrode assembly configured to receive a measurement substance for changing a capacitance of said electrode assembly,
  - a multi-frequency generator coupled to said electrode assembly and configured to supply in a timely ordered manner three or more signals each having a different frequency,
  - a sensing device connected to said electrode assembly and configured to determine a value indicative of the capacitance of said electrode assembly for each of said three or more different frequencies
  - a reference signal source configured to provide a reference signal to said sensing device, said reference signal representing respective reference values for each of said three or more different frequencies and being indicative of a respective capacitance of said electrode assembly for each of the three or more different frequencies for a reference state and
  - a communication unit configured to transmit date over a network; and
- the sensor system further comprises a central station having a control unit and communication means configured to receive data over said network, said control unit being configured to evaluate the states of the plurality of multi-frequency capacitive measurement devices on the basis of the data received therefrom.

21. The system of claim 20, wherein said plurality of multi-frequency capacitive measurement devices is positioned so as to be exposed to the conditions of a road surface.

22. The system of claim 20, wherein said communication means is further configured to receive meteorology data from an external source.

23. The system of claim 20, further comprising at least one further sensor element for obtaining environmental information.

24. A meteorology measurement system comprising:
- an electrode assembly configured to receive a measurement substance for changing a capacitance of said electrode assembly,
- a multi-frequency generator coupled to said electrode assembly and configured to supply in a timely ordered manner three or more signals each having a different frequency,
- a reference signal source configured to provide a reference signal to said sensing device, said reference signal representing respective reference values for each of said three or more different frequencies and being indicative of a respective capacitance of said electrode assembly for each of the three or more different frequencies for a reference state.
- a sensing device connected to said electrode assembly and configured to determine a value indicative of the capacitance of said electrode assembly for each of said three or more different frequencies,
- a control unit operatively connected to said multi-frequency capacitive measurement device and configured to evaluate data provided by said multi-frequency capacitive measurement device, and
- display means for displaying meteorology data.

25. A method of determining the state of an electrode assembly, the method comprising:
- supplying at least three signals of different frequency to said electrode assembly having a state of interest,
- determining a measurement value indicating a capacitance of the electrode assembly for each of the at least three different frequencies,
- comparing each measurement value with a respective library value for each of the at least three different frequencies, said library values representing a specified state of said electrode assembly for each of the at least three different frequencies, and
- identifying said state of interest as said specified state when each measurement value matches the respective library value within a predefined tolerance range;
- further comprising establishing a library of data representing a relative permittivity at each of said at least three different frequencies for at least said substance for a plurality of different states of said substance;
- further comprising applying said substance having a specified state on said electrode assembly, determining a reference measurement value indicating a capacitance of said electrode assembly for each of the at least three frequencies, and storing said reference measurement value or a value representing the same as library data for said specified state.

26. The method of claim 25, wherein said at least three different frequencies range from several Hz to several MHz.

27. The method of claim 25, further comprising exposing said electrode assembly to an environmental condition to receive at least one substance of interest, wherein said library values represent the state of said electrode assembly having applied thereon said at least one substance in a predefined state.

28. The method of claim 27, wherein said library values represent a relative permittivity of said at least one substance under specified conditions for each of the at least three different frequencies.

29. The method of claim 25, wherein said different states comprise a plurality of different temperatures of said substance.

30. The method of claim 25, wherein said library includes data representing the relative permittivity for each of the at least three different frequencies for a plurality of different substances.

31. The method of claim 25, wherein determining said measurement value indicating a capacitance of the electrode assembly for each of the at least three different frequencies comprises:
   a) charging said electrode assembly with a signal having one of said at least three different frequencies for a predefined time period,
   b) determining the charge stored on said electrode assembly, and
   c) repeating steps a) and b) for each of said at least three different frequencies.

32. The method of claim 31, wherein said predefined time period for each of the at least three different frequencies is adjusted by supplying a signal including a predefined number of pulses.

33. The method of claim 31, wherein said charge stored on said electrode assembly is determined by connecting said electrode assembly with a sense capacitor after said predefined time period and determining a voltage across said sense capacitor.

34. The method of claim 25, wherein determining said measurement value indicating a capacitance of the electrode assembly for each of the at least three different frequencies comprises:
   a) supplying a signal having one of said at least three different frequencies and a specified amplitude to said electrode assembly via a specified resistance,
   b) determining a voltage across said electrode assembly, and
   c) repeating steps a) and b) for each of said at least three different frequencies.

35. The method of claim 25, further comprising obtaining environmental information and identifying the state of electrode assembly on the basis of the environmental information.

36. The method of claim 35, wherein said environmental information comprises a temperature of an immediate environment of said electrode assembly.

37. A method of determining the state of an electrode assembly, the method comprising:
   supplying at least three signals of different frequency to said electrode assembly having a state of interest,
   determining a measurement value indicating a capacitance of the electrode assembly for each of the at least three different frequencies,
   comparing each measurement value with a respective library value for each of the at least three different frequencies, said library values representing a specified state of said electrode assembly for each of the at least three different frequencies, and
   identifying said state of interest as said specified state when each measurement value matches the respective library value within a predefined tolerance range;
   further comprising establishing a library of data representing a relative permittivity at each of said at least three different frequencies for at least said substance for a plurality of different states of said substance;
   wherein determining a measurement value indicating a capacitance of the electrode assembly for each of the at least three different frequencies further comprises generating a reference signal representing a reference state of said electrode assembly and subtracting said reference signal from an output signal of said electrode assembly to provide a differential signal for each of said at least three different frequencies.

38. The method of claim 37, wherein said reference signal is generated prior to said output signal when said electrode assembly is in said reference state and said reference signal or a representative thereof is stored.

39. The method of claim 38, wherein said reference signal or the representative thereof is stored in digital form and is converted into an analogous signal prior to being subtracted from said output signal.

* * * * *